(12) United States Patent
Jin et al.

(10) Patent No.: US 11,389,498 B2
(45) Date of Patent: Jul. 19, 2022

(54) ANTI-INFLAMMATORY COMPOSITION AND COMPOSITION FOR TREATMENT OF INFLAMMATORY DISEASE, BOTH COMPRISING COMPOSITE PLANT EXTRACT

(71) Applicant: KOREA ATOMIC ENERGY RESEARCH INSTITUTE, Daejeon (KR)

(72) Inventors: Chang-Hyun Jin, Jeollabuk-do (KR); Seung-Young Lee, Daegu (KR); Bo-Mi Nam, Jeollanam-do (KR); Yang-Kang So, Jeollabuk-do (KR); Dong-Sub Kim, Gwangju (KR); Si-Yong Kang, Daejeon (KR); Jin-Baek Kim, Gwangju (KR); Il-Yun Jeong, Daejeon (KR)

(73) Assignee: Korea Atomic Energy Research Institute, Daejeon (KR)

( * ) Notice: Subject to any disclaimer, the term of this patent is extended or adjusted under 35 U.S.C. 154(b) by 432 days.

(21) Appl. No.: 16/330,980

(22) PCT Filed: Sep. 20, 2017

(86) PCT No.: PCT/KR2017/010338
§ 371 (c)(1),
(2) Date: Mar. 6, 2019

(87) PCT Pub. No.: WO2018/056698
PCT Pub. Date: Mar. 29, 2018

(65) Prior Publication Data
US 2019/0255135 A1 Aug. 22, 2019

(30) Foreign Application Priority Data
Sep. 21, 2016 (KR) .......................... 10-2016-0120830

(51) Int. Cl.
| *A61K 36/535* | (2006.01) |
| *A61P 29/00* | (2006.01) |
| *A61K 36/254* | (2006.01) |
| *A61K 36/284* | (2006.01) |
| *A61K 36/53* | (2006.01) |

(52) U.S. Cl.
CPC .......... *A61K 36/535* (2013.01); *A61K 36/254* (2013.01); *A61K 36/284* (2013.01); *A61K 36/53* (2013.01); *A61P 29/00* (2018.01); *A61K 2236/15* (2013.01); *A61K 2236/33* (2013.01); *A61K 2236/37* (2013.01); *A61K 2236/51* (2013.01)

(58) Field of Classification Search
CPC .............. A61K 2300/00; A61K 36/284; A61K 36/535; A61K 2236/15; A61K 2236/33; A61K 2236/37; A61K 2236/51; A61K 36/254; A61K 36/53; A61P 29/00
See application file for complete search history.

(56) References Cited

U.S. PATENT DOCUMENTS

2015/0224159 A1   8/2015   Lo et al.

FOREIGN PATENT DOCUMENTS

| CN | 102964866 A | 3/2013 |
| CN | 103109740 A | 5/2013 |
| KR | 10-2009-0010186 A | 1/2009 |
| KR | 20130060950 A * | 6/2013 |
| KR | 10-2015-0106058 A | 9/2015 |
| WO | 2007/119984 A1 | 10/2007 |

OTHER PUBLICATIONS

Ahmed HW "Ethnomedicinal, Phytochemical and Pharmacological Investigations of Perilla frutescens (L.) Britt." Molecules, Dec. 28, 2018, 24(102), 23 pages; ; doi:10.3390/molecules24010102. (Year: 2018).*

Nam B, et al. "A New Monoterpene from the Leaves of a Radiation Mutant Cultivar of Perilla frutescens var. crispa with Inhibitory Activity on LPS-Induced NO Production" Molecules, Sep. 4, 2017, , 22, 1471; doi:10.3390/molecules22091471 (Year: 2017).*

Chang-Ho Kang et al., 'Inhibitory Effects of Aralia cordata Thunb Extracts on Nitric Oxide Synthesis in RAW 264.7 Macrophage Cells', Journal of Korean Society of Food Science and Technology, 2012, vol. 44, No. 5, pp. 621-627.

Qiu-Ye Lin et al., 'Inhibition of inducible nitric oxide synthase by Acanthopanax senticosus extract in RAW264.7 macrophages', Journal of Ethnopharmacology, 2008, vol. 118, pp. 231-236.

Mi-Hyeon Jang et al., 'Atractylodes japonica suppresses lipopolysaccharide-stimulated expressions of inducible nitric oxide synthase and cyclooxygenase-2 in RAW 264.7 macrophages', Biological and Pharmaceutical Bulletin, 2004, vol. 27, No. 3, pp. 324-327.

(Continued)

*Primary Examiner* — Aaron J Kosar
(74) *Attorney, Agent, or Firm* — Fox Rothschild LLP (57) ABSTRACT

The present invention relates to an anti-inflammatory composition and a composition for treatment of an inflammatory disease, both comprising a composite plant extract and, more particularly, to an anti-inflammatory composition comprising a composite plant extract including a *Perilla frutescens* extract and an *Atractylodes macrocephala* Koidzumi extract; a preparation method thereof; and a pharmaceutical composition comprising the composite extract for treatment of an inflammatory disease.

16 Claims, 7 Drawing Sheets

(56) References Cited

OTHER PUBLICATIONS

Ji et al. (Dec. 10, 2015) "Anti-inflammatory Activity of Atractylenolide III Through Inhibition of Nuclear Factor-KB and Mitogen-activated Protein Kinase Pathways in Mouse Macrophages", Immunopharmacology and Immunotoxicology, 38:98-102.

Ji et al. (Oct. 1, 2014) "Atractylenolide I Inhibits Lipopolysaccharide-Induced Inflammatory Responses via Mitogen-activated Protein Kinase Pathways in RAW264.7 Cells", Immunopharmacology and Immunotoxicology, 36:420-425.

* cited by examiner

ORAL ADMINISTRATION OF EXTRACT MIXTURE OF EMBODIMENT 1 TO ARTHRITIS

| NORMAL MOUSE | ARTHRITIC MOUSE | 25mg/kg | 50mg/kg | 100mg/kg |

(a)

| NORMAL MOUSE | ARTHRITIC MOUSE | ORAL ADMINISTRATION OF EXTRACT MIXTURE OF EMBODIMENT 6 TO ARTHRITIS 66.5mg/kg | ORAL ADMINISTRATION OF EXTRACT MIXTURE OF EMBODIMENT 6 TO ARTHRITIS 133.0mg/kg |

ANTI-INFLAMMATORY COMPOSITION AND COMPOSITION FOR TREATMENT OF INFLAMMATORY DISEASE, BOTH COMPRISING COMPOSITE PLANT EXTRACT

CROSS-REFERENCES TO RELATED APPLICATIONS

This application is a 35 U.S.C. § 371 of U.S. national entry of International Application PCT/KR2017/010338, having an International filing date of Sep. 20, 2017, which claims under 35 U.S.C. § 119 the benefit of Korean Patent Application 10-2016-0120830 filed on Sep. 21, 2016 in the Republic of Korea. The entire contents of these applications are incorporated herein by reference in their entirety.

TECHNICAL FIELD

The present disclosure relates to an anti-inflammatory composition comprising a natural phyto-extract mixture, and more particularly, to an anti-inflammatory composition comprising a *Perilla frutescens* Britt. extract and an *Atractylodes japonica* Koidz. extract, and a pharmaceutical composition for the treatment of inflammatory diseases.

BACKGROUND ART

Inflammation is a topical protective response caused by injury or destruction of tissue, which acts to destroy, weaken or shield both injurious substances and injured tissues. The characteristic of inflammation is that microvessels are perforated, blood components leak into interstitial space, and white blood cells migrate to the inflamed tissue. On a macroscopic aspect, it is usually accompanied by clinical symptoms such as erythema, edema, hyperalgesia, pain and the like.

An inflammatory response is any response which is characterized by inflammation, as defined above. The inflammatory response causes a large amount of the physical discomfort associated with different diseases and injuries, such as pain and loss of function, which is well-known in the medical field. Accordingly, to administer a pharmaceutical agent reducing the physical discomfort of the inflammatory response is preferred, and an agent having this property is classified as anti-inflammatory. Anti-inflammatory drugs are used for the treatment of a wide variety of diseases, and the same drugs may often be used for the treatment of different diseases.

As an anti-inflammatory substance, natural and synthetic corticosteroid agents may cause a number of side effects, including increased blood pressure, salt and water stagnation, kidney damage, and increased potassium and calcium secretion. On the other hand, nonsteroidal anti-inflammatory drugs (NSAID) have been developed to overcome the side effects of such steroidal substances. Among the NSAIDs, salicylate is the most widely used, and acetylsalicylic acid or aspirin is the most widely used analgesic, antipyretic and an anti-inflammatory substance, and is disclosed in Korean Patent Application No. 2008-7027164. However, when administered in large amounts, various side effects such as respiratory stimulation, circulatory collapse, upper abdominal pain, vomiting, gastrointestinal bleeding, liver damage, platelet inhibition and the like may be caused, which is known in the art.

As such, while many types of anti-inflammatory substances are used, a need for a substance having no side effects and having anti-inflammatory properties remains required.

Therefore, when a natural anti-inflammatory agent having excellent anti-inflammatory activity and being safe for the human body is developed, such an anti-inflammatory agent may be expected to be usefully applied in the related field.

DISCLOSURE

Technical Problem

An aspect of the present disclosure is to provide an anti-inflammatory composition comprising a phyto-extract mixture which is excellent in terms of anti-inflammatory activity and safe for the human body.

Another aspect of the present disclosure is to provide a manufacturing method of an anti-inflammatory composition comprising a phyto-extract mixture which is excellent in terms of anti-inflammatory activity and safe for the human body.

Another aspect of the present disclosure is to provide a pharmaceutical composition for the treatment of inflammatory diseases comprising a phyto-extract mixture which is excellent in anti-inflammatory activity and safe for the human body.

Technical Solution

According to an aspect of the present disclosure, an anti-inflammatory composition comprising a phyto-extract mixture including a *Perilla frutescens* Britt. extract and an *Atractylodes japonica* Koidz. extract is provided.

According to another aspect of the present disclosure, a manufacturing method of an anti-inflammatory composition comprising obtaining phyto-extracts, including obtaining a *Perilla frutescens* Britt. extract and obtaining an *Atractylodes japonica* Koidz. extract; and manufacturing an extract mixture by mixing respectively obtained phyto-extracts is provided.

According to another aspect of the present disclosure, a pharmaceutical composition for the treatment of inflammatory diseases comprising a phyto-extract mixture including a *Perilla frutescens* Britt. extract and an *Atractylodes japonica* Koidz. extract is provided.

Advantageous Effects

Since the anti-inflammatory composition and the pharmaceutical composition for the treatment of inflammatory diseases according to the present disclosure may treat, prevent and improve a wide range of inflammations by using an extract mixture consisting of a mixture of extracts obtained from a *Perilla frutescens* Britt. having excellent content of isoegomaketone and an *Atractylodes japonica* Koidz., it may be expected to be usefully used for anti-inflammatory purposes in various fields such as cosmetics, heath functional foods, medicines, daily necessities, and the like.

BEST MODE FOR INVENTION

Hereinafter, exemplary embodiments of the present disclosure will be described with reference to the accompanying drawings. The disclosure may, however, be exemplified in many different forms and should not be construed as being limited to the specific embodiments set forth herein.

According to the present disclosure, an anti-inflammatory composition including a phyto-extract mixture including a *Perilla frutescens* BRITT. extract and an *Atractylodes japonica* Koidz. extract is provided. In addition, an Acanthopanaxsenticosus extract may be further included, if necessary, for the present disclosure.

In the present disclosure, a rootstock of the *Atractylodes japonica* Koidz. can be used and it is known that the *Atractylodes japonica* Koidz. has an efficacy in strengthening the spleen and providing energy, taking up moisture to allow urine to flow smoothly, stopping sweating, and stabilizing the fetus of pregnant women. In addition, it is known that the *Atractylodes japonica* Koidz. is used for the treatment of symptoms such as eating not much having no appetite due to weak spleen, diarrhea, a symptom of dizziness when eating food with sputum or asthma, dropsy, hyperhidrosis, an unstable symptom of fetal movement in pregnant women.

The Acanthopanaxsenticosus is a deciduous broad-leaved shrub belonging to the araliaceae family of plants, and a bark can be used for making the phyto-extract, and an Acanthopanaxsenticosus may be called as Siberian *Ginseng*, since its appearance resembles wild *ginseng*. It is known that the Acanthopanaxsenticosus tree contains a large amount of acanthoside with excellent biological activity and various useful components and is used for neuralgia, hypertension, nervous breakdowns, diabetes, tonics, and the like.

In addition, the *Perilla frutescens* Britt is an annual herb of Labiatae family, and the leaves from the *Perilla frutescens* Britt can be used for making the phyto-extract, and it is used for sweating, antitussive, stomachic, diuretic, sedative and analgesic, and is known to be effective for the treatment of dizziness, body pain, nasal congestion, and runny nose.

The *Perilla frutescens* Britt. extract used in the present disclosure contains isoegomaketone (IK) or a salt thereof as an active ingredient, and, in particular, the *Perilla frutescens* Britt. extract used in the present disclosure may have an isoegomaketone (IK) content of 10 mg to 30 mg per 1 g of the extract, and has an isoegomaketone (IK) concentration of 100 mg/mL to 300 mg/mL.

When the *Perilla frutescens* Britt. extract of the present disclosure has an isoegomaketone (IK) content of less than 10 mg per 1 g of the extract or an isoegomaketone (IK) concentration of less than 100 mg/mL, the desired anti-inflammatory effect may be insufficient, and toxicity tends to be increased when the *Perilla frutescens* Britt. extract has an isoegomaketone (IK) content of more than 30 mg per 1 g of the extract or an isoegomaketone (IK) concentration of more than 300 mg/mL.

The *Perilla frutescens* Britt. in which the isoegomaketone (IK) content is increased may be obtained by irradiation with, for example, radiation, in the range of 50 to 500, in detail, gamma rays of 150 to 250 Gy, in more detail, gamma rays of about 200 Gy.

Figure 1:
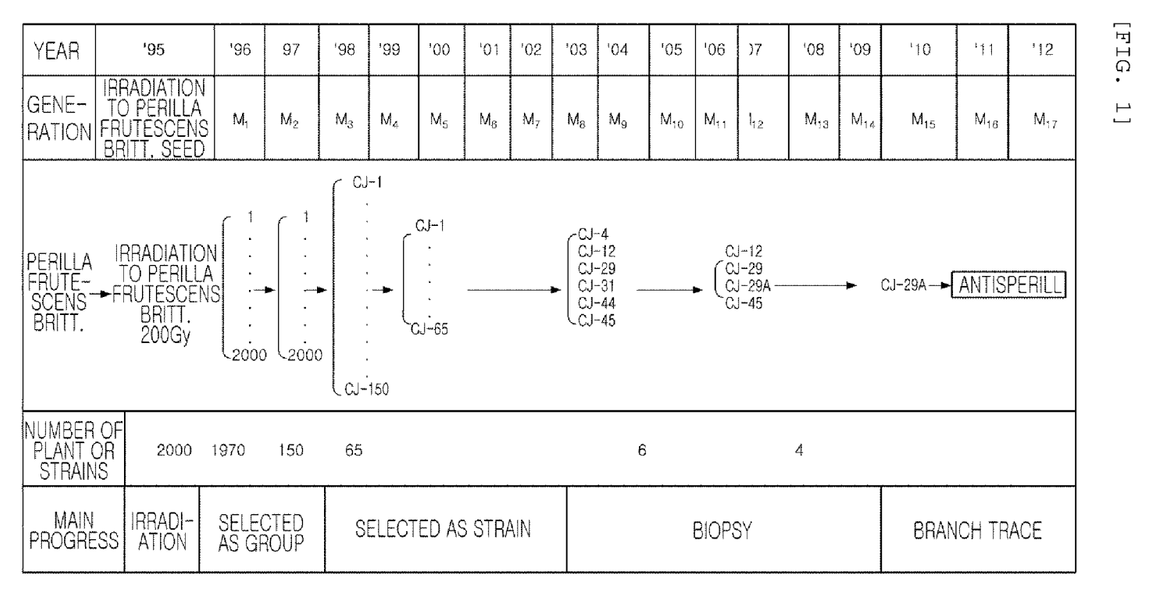
FIG. 1 illustrates a preparing process of an Antisperill, a *Perilla frutescens* Britt., which may be used in the present disclosure.

FIG. 1 illustrates an exemplary preparing process of Antisperill. More specifically, after irradiating the *Perilla frutescens* Britt. seeds with the radiation, selecting those with excellent growth in M1 generation and growing to M3 generation and after confirming that the traits are fixed and final 150 pieces may be systematized, CJ-29A, which has excellent anti-inflammatory efficacy through evaluation of physiological activity may be selected, and in this case, the selection process may proceed mainly with excellent growth.

Antisperill, thus obtained, was deposited with the Korean Collection for Type Cultures, KCTK on Aug. 17, 2016 and was given the deposit number KCTC 13077BP.

In the present specification, the *Perilla frutescens* Britt. having an increased isoegomaketone (IK) content may be Antisperill, which was given the deposit number of KCTC 13077BP.

On the other hand, the extract mixture of the present disclosure means that the phyto-extract such as a *Perilla frutescens* Britt. extract, an *Atractylodes japonica* Koidz. extract, and the like are independently prepared and then mixed.

In addition, in the present disclosure, the *Perilla frutescens* Britt. extract, the *Atractylodes japonica* Koidz. extract and the Acanthopanaxsenticosus extract may be respectively extracted with an ethanol solvent, in detail, the ethanol solvent has an ethanol concentration of 60% or more, in more detail, the ethanol solvent has an ethanol concentration of 100%. In the case of performing extraction using an ethanol solvent, as illustrated in FIG. 4, a remarkably improved anti-inflammatory effect may be obtained.

Figure 3:
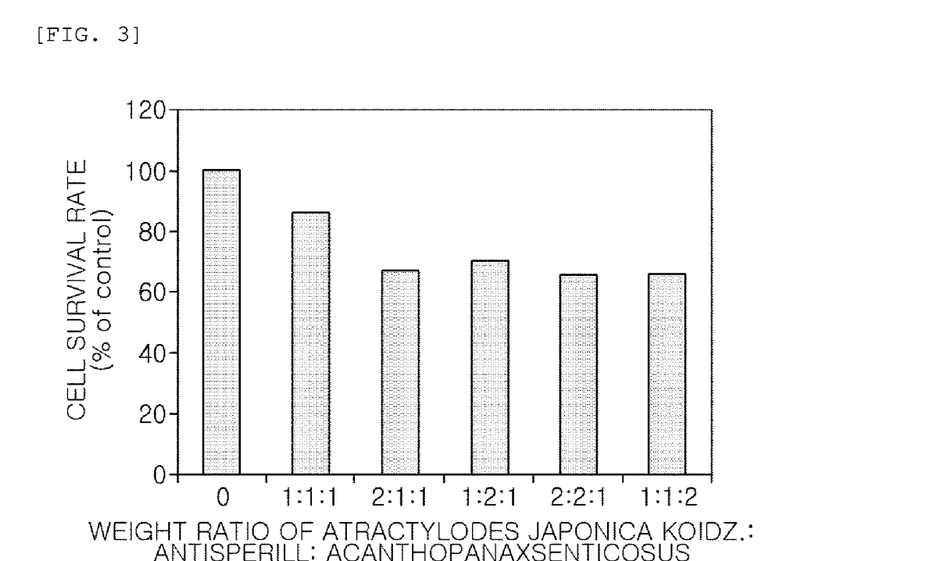
FIG. 3 illustrates a result of measuring a degree of toxicity of an extract mixture.

At this time, the phyto-extract mixture may be obtained by mixing the weight of the other two extracts per 1 part by weights of the extract of any one of the *Perilla frutescens* Britt. extract, the *Atractylodes japonica* Koidz. extract and the Acanthopanaxsenticosus extract with 1 part by weight to 2 parts by weight, respectively. In more detail, the phyto-extract mixture is obtained by mixing the *Perilla frutescens* Britt. extract, the *Atractylodes japonica* Koidz. extract and the Acanthopanaxsenticosus extract at a weight ratio of about 1:1:1. When the *Perilla frutescens* Britt. extract, the *Atractylodes japonica* Koidz. extract and the Acanthopanaxsenticosus extract is mixed at a weight ratio of about 1:1:1, as shown in FIG. 3, toxicity may be remarkably lowered, as compared to the other mixing ratios.

On the other hand, the *Perilla frutescens* Britt. extract and the *Atractylodes japonica* Koidz. extract may be obtained by supercritical extraction, respectively, when the extracts are obtained by a supercritical extraction method from the *Perilla frutescens* Britt., the isoegomaketone (IK) content is increased by about 7 times, as compared with an alcohol extraction using an ethanol, and when the extract is obtained by a supercritical extraction method from the *Atractylodes japonica* Koidz., the content of atlactylenolide is also remarkably increased. In other words, when supercritical extraction is used, extracts of different composition from an ethanol extract may be obtained, as a result, a remarkable anti-inflammatory effect may be obtained without addition of the Acanthopanaxsenticosus extract, and the like.

According to the present disclosure, a manufacturing method of an anti-inflammatory composition including the phyto-extract mixture is performed by including obtaining phyto-extracts, including obtaining the *Perilla frutescens* Britt. extract, and obtaining the *Atractylodes japonica* Koidz. extract, and manufacturing an extract mixture by mixing respectively obtained phyto-extracts.

Respectively obtaining the phyto-extracts may be performed by including lyophilizing each plant, pulverizing the lyophilized plant, and blending the lyophilized plant with an ethanol solvent, independently and extracting the lyophilized plant, and in this case, the phyto-extract may further include the Acanthopanaxsenticosus extract.

In this case, respectively washing the *Perilla frutescens* Britt., the *Atractylodes japonica* Koidz., the acanthopanaxsenticosus, and the like may be further included to remove contaminants before performing the lyophilization operation, the lyophilization operation may be performed subsequently to respectively wash the *Perilla frutescens* Britt., the *Atractylodes japonica* Koidz. and the Acanthopanaxsenticosus.

In the present disclosure, the lyophilization operation may be performed under conventional conditions in the art, and the lyophilization operation is preferable because it has excellent drying efficiency and no residual solvent.

The extraction operation may be performed after pulverizing lyophilized plants. When the lyophilized plant is pulverized, it is advantageous that quantitative measurement in the future is easy and has no residual solvent.

Further, respectively obtaining the phyto-extracts may be performed by the supercritical extraction of each plant, and in this case, an anti-inflammatory composition having an improved anti-inflammatory effect may be obtained.

On the other hand, according to the present disclosure, a pharmaceutical composition for the treatment of inflammatory diseases, which comprises the phyto-extract mixture including a *Perilla frutescens* Britt. extract, an *Atractylodes japonica* Koidz. extract, is provided.

The phyto-extract mixture may include alcohol extracts of each plant, in this case, the phyto-extract mixture may further include an Acanthopanaxsenticosus extract. On the other hand, the phyto-extract mixture may include supercritical extracts of each plant, and a pharmaceutical composition for the treatment of inflammatory diseases having a remarkably increased anti-inflammatory effect may be obtained.

According to the present disclosure, the inflammatory disease is selected from the group consisting of asthma, chronic obstructive pulmonary disease (COPD), allergic rhinitis, dermatitis, arthritis, allergies and inflammatory bowel disease, and especially, arthritis is rheumatoid arthritis.

Further, the pharmaceutical composition may further include a pharmaceutically acceptable carrier or excipient.

The pharmaceutical composition for the treatment of inflammatory diseases according to the present disclosure may be formulated into various forms, such as oral formulations such as powders, granules, tablets, capsules, suspensions, emulsions, syrups, aerosols, and the like, types of sterilized injection solutions, and the like, according to a conventional methods for each purpose of use, and may be administered by various routes including oral administration or intravenous, intraperitoneal, subcutaneous, rectal, topical administration, and the like.

Examples of suitable carriers, excipients and diluents that may be included in the pharmaceutical composition for the treatment of inflammatory diseases include lactose, dextrose, sucrose, sorbitol, mannitol, xylitol, erythritol, maltitol, starch, acacia rubber, alginate, gelatin, calcium phosphate, calcium silicate, cellulose, methylcellulose, amorphous cellulose, polyvinylpyrrolidone, water, methylhydroxybenzoate, propylhydroxybenzoate, talc, magnesium stearate, mineral oil, and the like.

In addition, the pharmaceutical composition for the treatment of inflammatory diseases may further include a filler, an anticoagulant, a lubricant, a wetting agent, a flavoring agent, an emulsifying agent, an antiseptic, and the like.

Solid formations for oral administration include tablets, pills, powders, granules, capsules, and the like, which may be formulated by mixing at least one excipient such as starch, calcium carbonate, sucrose, lactose, gelatin and the like in the pharmaceutical composition for the treatment of inflammatory diseases. In addition to simple excipients, lubricants such as magnesium stearate and talc may also be used.

Examples of oral liquid formations include suspensions, solutions, emulsions, syrups, and the like, in addition to water and liquid paraffin, which are commonly used diluents, various excipients such as wetting agents, sweeteners, fragrances, preservatives, and the like may be included.

Formations for parenteral administration include sterile aqueous solutions, non-aqueous solvents, suspensions, emulsions, lyophilized formations and suppositories.

Non-aqueous solvents and suspensions may include propylene glycol, polyethylene glycol, vegetable oils such as olive oil, injectable esters such as ethyloleate, and the like. Base materials for injections may include conventional additives such as solubilzers, isotonic agents, suspending agents, emulsifying agents, stabilizing agents and preservatives.

By administering the composition of the present disclosure to a patient, preventing and treating inflammatory diseases is possible by inhibiting and improving progression and deepening of inflammation in inflammatory diseases. The pharmaceutical composition for the treatment of inflammatory diseases of the present disclosure is administered in a pharmaceutically effective amount.

The composition of the present disclosure may be administered as an individual therapeutic agent or in combination with other therapeutic agents, sequentially or concurrently with conventional therapeutic agents, and may be administered singly or multiply. It is important to take into account all of the above factors and to administer the amount in which the maximum effect may be obtained in a minimal amount without side effects, which may be easily determined as required.

Specifically, the pharmaceutically effective amount of compound according to the present disclosure may vary depending on the age, gender and body weight of the patient, and is generally 1 to 50 mg, in detail, 1 to 10 mg per kg of body weight may be administered per day or every other day or one to three divided doses per day.

However, the dosage is not limited to the scope of the present disclosure by any means since the dosage may be varied depending on the administration route, severity of disease, gender, body weight, age, and the like.

Hereinafter, the present disclosure will be described more specifically with reference to detailed exemplary embodiments. The following exemplary embodiments are merely examples for easier understanding of the present disclosure, and the scope of the present disclosure is not limited thereto.

INDUSTRIAL APPLICABILITY

Embodiment

1. Manufacturing of *Perilla frutescens* Britt. in which the Isoegomaketone (IK) Content is Increased The *Perilla frutescens* Britt. extract of the present disclosure has an isoegomaketone (IK) content of more than 10 mg per 1 g of the *Perilla frutescens* Britt. extract, and is obtained from a *Perilla frutescens* Britt. having an IK concentration of 100 mg/mL or more. Such a *Perilla frutescens* Britt. having a high content of IK was obtained by the following preparing process.

In 1995, 2000 seeds of the *Perilla frutescens* Britt. were gathered after irradiation with 200 Gy of gamma rays The seeds gathered from 2000 pieces in the M1 generation were cultivated, 150 pieces thereof were systematized and a systematized name was given in the M3 generation. To test the uniformity and stability of the 150 strains selected on the basis of the excellent growth in the M9 generation, six strains with excellent agronomic traits were selected after cultivating 30 pieces for each strain, thereafter a CJ-29A strain, having an increased isoegomaketone content, which has an excellent effect for anti-inflammation, was selected through analysis of components of the selected six strains. At this time, basically, a strain which has excellent growth was selected and the CJ-29A strain shows the highest activity as a result of measuring the anti-inflammatory physiological activity using the selected strain and metabolism analysis showed that isoegomaketone was increased. After that, the CJ-29A strain was given the name "Antisperill", and the quantity test and regional adaption test were conducted in the Korea Atomic Energy Research Institute Advanced Radiation Technology Institute breeding test center. FIG. 1 systematically illustrates progress of preparation of the "Antisperill".

Antisperill, thus obtained, was deposited with the Korean Collection for Type Cultures (KCTK) on Aug. 17, 2016 and received the deposit number of KCTC 13077BP.

2. Preparation of Extract Mixture

Preparation Example 1

(1) Preparation of a *Perilla frutescens* Britt. Alcohol Extract

The *Perilla frutescens* Britt. leaves obtained in the 1. Manufacturing of *Perilla frutescens* Britt. in which the isoegomaketone (IK) content is increased were dried at about 45° C. and pulverized, and 10 g of the dried powder sample of the *Perilla frutescens* Britt. was extracted with using 100 mL of fermentation alcohol (100% ethanol) at 45° C. and 100 rpm for 6 hours in an extraction apparatus (product name: SI-600R, manufactured by JeioTech) by using an agitation extraction method.

The thus obtained extract was filtered with a filter paper, concentrated using a rotary vacuum concentrator (product name: N-1100, manufactured by: EYELA) and then the solvent was removed using a high-efficiency centrifugal concentrator (product name: HT-4X, manufactured by GeneVac) to obtain the *Perilla frutescens* Britt. extract.

(2) Preparation of an *Atractylodes japonica* Koidz. Extract and/or an Acanthopanaxsenticosus Alcohol Extract 10 g of each of Acanthopanaxsenticosus and *Atractylodes japonica* Koidz. samples, dried and pulverized at about 45° C., were extracted using 100 mL of fermentation alcohol (100% ethanol) at 100 rpm, at 60° C. by using a agitated extraction method (product name: SI-600R, manufactured by JeioTech) for 6 hours.

The thus obtained Acanthopanaxsenticosus extract and *Atractylodes japonica* Koidz. extract were respectively filtered with a filter paper and then concentrated using a rotary vacuum concentrator (product name: N-1100, manufactured by EYELA) and a solvent was completely removed using a high-efficiency centrifugal concentrator (product name: HT-4X, manufactured by GeneVac) to obtain each of the Acanthopanaxsenticosus extract and the *Atractylodes japonica* Koidz. extract.

Preparation Example 2

Except that 70% ethanol was used as a solvent in extracting the *Perilla frutescens* Britt., the Acanthopanaxsenticosus and the *Atractylodes japonica* Koidz., the extracts of the *Perilla frutescens* BRITT., the Acanthopanaxsenticosus and *Atractylodes japonica* Koidz. were respectively obtained by the same process of Preparation Example 1

Preparation Example 3

(1) Preparation of a *Perilla frutescens* Britt. Supercritical Extract

The leaves of "Antisperill" *Perilla frutescens* Britt. obtained in the 1. Manufacturing of *Perilla frutescens* Britt. in which the isoegomaketone (IK) content is increased were harvested and dried in a dryer at 50° C. for 24 hours and then crushed to prepare a powder. Extraction was performed using 200 of prepared *Perilla frutescens* Britt. powder using the supercritical fluid extraction equipment (ILSIN AUTOCLAVE, ISA-SEFE-0500-0700-080), under specific extraction conditions as shown in Table 1 below.

TABLE 1

| Extractor | | Assisted | Separator | | | | |
|---|---|---|---|---|---|---|---|
| Pressure (bars) | Temperature (° C.) | solvent flux (ml/min) | Pressure (bars) | Temperature (° C.) | $CO_2$ flux (ml/min) | Cooler (° C.) | Run-time (mins) |
| 400 | 50 | — | 40 | 40 | 550/12 | 1 | 180 |

Figure 2:
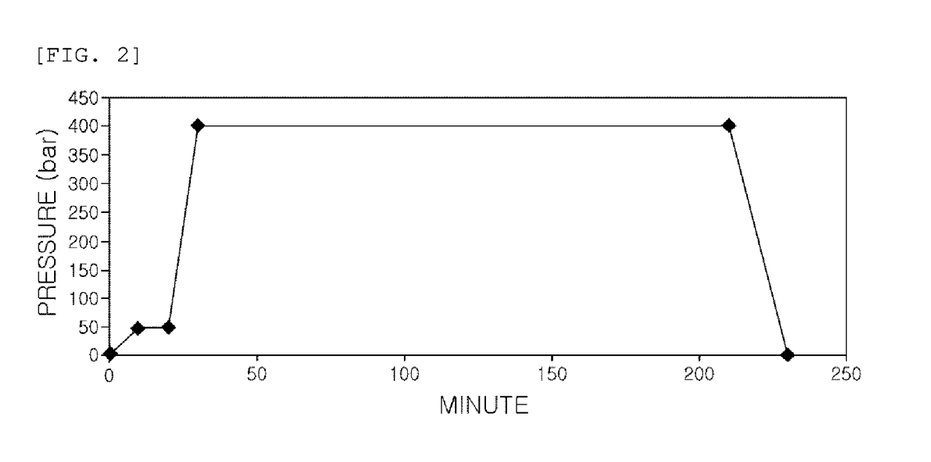
FIG. 2 illustrates a supercritical extraction process, which shows pressure change over time.

The extraction process was performed as shown in FIG. 2 by isobaric process for 10 minutes, purging for 10 minutes, pressurization for 10 minutes, extraction at 400 bars of pressure for 180 minutes and decompression for 20 minutes. After removing water from the supercritical extract, the final extract was obtained.

(2) Preparation of an *Atractylodes japonica* Koidz. Extract

Dried *Atractylodes japonica* Koidz. for food were purchased and crushed into powder form. Extraction was performed using the supercritical fluid extraction equipment (ILSIN AUTOCLAVE, ISA-SEFE-0500-0700-080) using 200 g of prepared *Atractylodes japonica* Koidz. powder under the same conditions as the (1) Preparation of a *Perilla frutescens* Britt. supercritical extract. After removing moisture from the supercritical extract, the final extract was obtained.

Comparative Preparation Example 1

The extracts of *Perilla frutescens* Britt., Acanthopanaxsenticosus and *Atractylodes japonica* Koidz. were respectively obtained by the same process as in the Production Example 1, except that water was used as a solvent in extracting the *Perilla frutescens* Britt., the Acanthopanaxsenticosus and the *Atractylodes japonica* Koidz.

(3) Preparation of an Extract Mixture

Example 1

The extract mixture of the present disclosure was prepared by mixing the *Atractylodes japonica* Koidz., Antisperill and Acanthopanaxsenticosus extracts respectively obtained in the preparation Example 1 at a weight ratio of 1:1:1.

Example 2

The extract mixture of the present disclosure was prepared by mixing the *Atractylodes japonica* Koidz., Antisperill and Acanthopanaxsenticosus extracts respectively obtained in the preparation Example 1 at a weight ratio of 2:1:1.

Example 3

The extract mixture of the present disclosure was prepared by mixing the *Atractylodes japonica* Koidz., Antisperill and Acanthopanaxsenticosus extracts respectively obtained in the preparation Example 1 at a weight ratio of 1:2:1.

Example 4

The extract mixture of the present disclosure was prepared by mixing the *Atractylodes japonica* Koidz., Antisperill and Acanthopanaxsenticosus extracts respectively obtained in the preparation Example 1 at a weight ratio of 2:2:1.

Example 5

The extract mixture of the present disclosure was prepared by mixing the *Atractylodes japonica* Koidz., Antisperill and Acanthopanaxsenticosus extracts respectively obtained in the preparation Example 1 at a weight ratio of 1:1:2.

Example 6

The extract mixture of the present disclosure was prepared by mixing the *Atractylodes japonica* Koidz. and Antisperill extracts respectively obtained in the preparation Example 3 at a weight ratio of 1:1.

3. Quantitative Analysis of Isoegomaketone in *Perilla frutescens* Britt. Extract A HPLC (Agilent Technologies) was used for the analysis of isoegomaketone in the *Perilla frutescens* Britt. extract obtained in (1) of the preparation Example 1 and common *Perilla frutescens* Britt. extract. The operating conditions for the quantitative analysis are shown in Table 2 below.

TABLE 2

| Column | ZORBAX eclipse XDB-C18 |
|---|---|
| Detection | 254 nm (DAD1) |
| Velocity | 1 mL/min. |
| Temperature | 27° C. |
| Solvent A | 5% Acetic acid (Water) |
| Solvent B | 5% Acetic acid (Acetonitrile) |

| | Time | B (%) |
|---|---|---|
| Gradient | 0 | 10 |
| | 40 | 30 |
| | 42 | 100 |
| | 45 | 100 |
| | 47 | 10 |
| | 60 | 10 |

The results of analysis of isoegomaketone in *Perilla frutescens* Britt. extract obtained in (1) of the preparation Example 1 and common *Perilla frutescens* Britt. extract are shown in Table 3 below.

TABLE 3

| Species | Harvest time | IK concentration (mg/mL) | IK (mg)/extracts (g) |
|---|---|---|---|
| Antisperill | July 23 | 212.74 | 21.27 |
| | | 203.20 | 20.87 |
| | | 216.16 | 21.98 |
| | August 26 | 102.71 | 10.27 |
| | | 102.58 | 10.26 |
| | | 106.55 | 10.65 |

TABLE 3-continued

| Species | Harvest time | IK concentration (mg/mL) | IK (mg)/extracts (g) |
|---|---|---|---|
| | September 23 | 215.53 | 21.55 |
| | | 236.92 | 23.69 |
| | | 232.93 | 23.29 |
| Wild *Perilla frutescens* BRITT. | July 23 | 26.60 | 2.66 |
| | | 20.96 | 2.09 |
| | | 21.03 | 2.10 |
| | August 26 | 73.30 | 7.33 |
| | | 73.85 | 7.39 |
| | | 71.21 | 7.12 |
| | September 23 | 6.37 | 0.64 |
| | | 6.36 | 0.64 |
| | | 6.48 | 0.65 |

As can be seen from the Table 3, in the case of *Perilla frutescens* Britt. obtained in (1) of Preparation Example 1, isoegomaketone (IK) is more than 10 mg per 1 g of *Perilla frutescens* Britt. extract, concentration is more than 100 mg/mL, it may be confirmed that the content of isoegomaketone is increased about 40 times as compared with the common wild *Perilla frutescens* Britt.

4. Quantitative Analysis of Active Ingredients in Extracts According to an Extraction Method (1) *Perilla frutescens* Britt. Extract 1 ml of methanol was taken in 1 mg of the *Perilla frutescens* BRITT. supercritical extract obtained in (1) of the Preparation Example 3 and filtered through a 0.45 μm filter, which was analyzed using HPLC (Agilent technology). The operating conditions for the quantitative analysis are shown in Table 4 below.

TABLE 4

| Column | YMC-Triart C18 250×4.6 mm, S-5um, 12 nm |
|---|---|
| Detection | 254 nm |
| Velocity | 1 ml/min |
| Temperature | 25° C. |
| Solvent A | Water |
| Solvent B | Acetonitrile |

| | Time (min) | B (%) |
|---|---|---|
| Gradient | 0 | 45 |
| | 30 | 55 |

As a result, when the extract was obtained from *Perilla frutescens* BRITT. by the supercritical extraction method, as shown in Table 5 below, it could be confirmed that the content of isoegomaketone was increased about 7 times as compared with the common alcohol extraction.

TABLE 5

| | Alcohol extraction (Preparation Example 1) | Supercritical extraction (Preparation Example 3) |
|---|---|---|
| Content of isoegomaketone in *Perilla frutescens* BRITT. | 9-10 mg/g | 75-76 mg/g |

(2) *Atractylodes japonica* Koidz. Extract

When the extract was obtained from the *Atractylodes japonica* Koidz. obtained in (2) of the Preparation Example 3 by the supercritical extraction method, as shown in Table 6, it could be confirmed that the content of atlactylenolide was doubled as compared with the common alcohol extraction.

TABLE 6

| | Alcohol extraction (Preparation Example 1) | Supercritical extraction (Preparation Example 3) |
|---|---|---|
| Content of atractylenolide in *Atractylodes japonica* Koidz. | 3-4 mg/g | 8.2~8.5 mg/g |

5. Cytotocixity Test of Extract Mixture

RAW264.7 cells, which are mouse inflammatory cells, were cultured in 96 wells at a concentration of $2.0 \times 10^5$ cell/ml in a 37° C., 5% $CO_2$ atmosphere for 24 hours. Then, each of the extract mixtures obtained in Examples 1 to 5 were processed at a concentration 50 μg/ml. After further incubation for 24 hours, a degree of cytotoxicity was measured by using EZ-Cytox (Daeil Lab Service) kit.

The results of measuring the degree of toxicity of each of the extract mixtures are shown in FIG. 3, as shown in FIG. 3, it could be confirmed that the extract mixtures respectively mixing the extracts of *Atractylodes japonica* Koidz., *Perilla frutescens* Britt. and Acanthopanaxsenticosus showed acceptable degree of toxicity as compared to the untreated control, in particular, the extract mixture of Example 1 in which the respective extracts were mixed at the same weight ratio, toxicity was remarkably lower than that of other blending ratio by 10% or more.

6. Evaluation of Anti-Inflammatory Efficacy (1) Evaluation of Anti-Inflammatory Efficacy of Each Extract An anti-inflammatory efficacy was assessed by measuring whether nitric oxide (NO), one of the markers of inflammatory response was produced. RAW 264.7 cells, which are mouse inflammatory cells were cultured in 96 wells at a concentration of $2.0 \times 10^5$ cell/ml in a 5% $CO_2$ and at 37° C. environment for 24 hours and then each of the extracts was treated at a concentration of 50 μg/ml. After 2 hours of culture, LPS was treated at 1 μg/ml, then incubated for 18 hours and an amount of NO produced was measured using a Griess reagent.

At this time, the above experiment was carried out on each of the extracts of *Atractylodes japonica* Koidz., *Perilla frutescens* Britt., and Acanthopanaxsenticosus obtained in the Preparation Example 1, the Preparation Example 2 and the Comparative Preparation Example 1, and were also carried out in each of the extracts of *Atractylodes japonica* Koidz. and *Perilla frutescens* Britt. of Preparation Example 3, respectively.

Figure 4A:
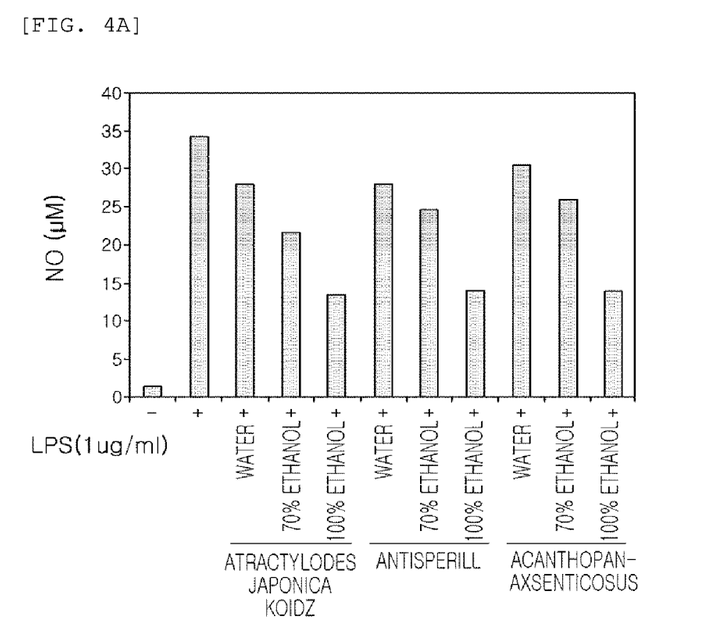
FIG. 4 illustrates a result (a) of measuring an amount of NO produced when each of alcohol extracts was treated to cells and a result of (b) of measuring an amount of NO produced when each of the supercritical extracts of the *Atractylodes japonica* Koidz. extract and the *Perilla frutescens* Britt. extract was treated to cells, to evaluate each of the anti-inflammatory efficacy of the *Atractylodes japonica* Koidz. extract and the *Perilla frutescens* Britt. extract.

The results of measurement of the amount of NO produced when the respective extracts were treated are shown in FIG. 4, as can be seen from FIG. 4A, it could be confirmed that all extracts of the *Atractylodes japonica* Koidz., *Perilla frutescens* Britt. and Acanthopanaxsenticosus may obtain a remarkable anti-inflammatory effect in the case of using an ethanol (alcohol) solvent as in Preparation Examples 1 and 2 as compared with the case of using water as in Comparative preparation Example 1. Further, it could be confirmed that a more effective anti-inflammatory effect may be obtained when the 100% ethanol of Preparation Example 1 is used as a solvent than when 70% ethanol of Preparation Example 2 is used as a solvent.

Figure 4B:
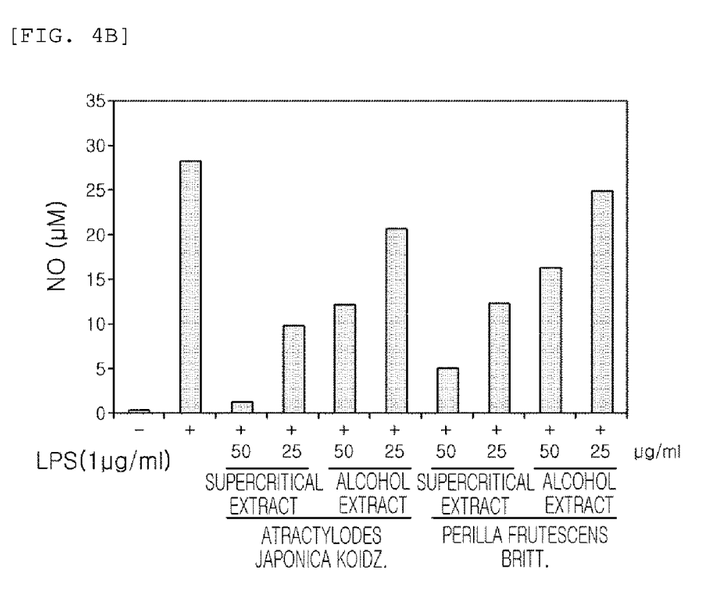

Further, as can be seen from FIG. 4B, it could be confirmed that when the extract was obtained by supercritical extraction as in Preparation Example 3, a more remarkable anti-inflammatory effect may be obtained.

In FIG. 4, negative control used RAW 264.7 cells which were not treated with any extract, and positive control used RAW 264.7 cells which were treated with LPS.

(2) Evaluation of Anti-Inflammatory Efficacy of Extract Mixture

The anti-inflammatory efficacy was assessed by measuring whether nitric oxide (NO), one of the markers of inflammatory response was produced. RAW 264.7 cells, which are mouse inflammatory cells, were cultured in 96 wells at a concentration of $2.0 \times 10^5$ cell/ml, in a 5% $CO_2$ atmosphere for 24 hours and then treated with the extract mixture of Example 1 at a concentration of 50 µg/ml. After 2 hours of culture, LPS was treated at a concentration of 1 µg/m, then additionally incubated for 18 hours and the amount of NO produced was measured using a Griess reagent.

Figure 5:
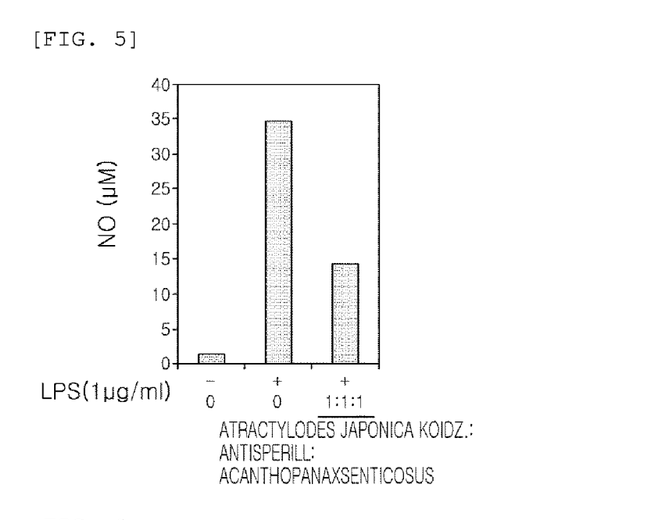
FIG. 5 illustrates a result of measuring an amount of NO produced when the extract mixture of an exemplary embodiment was treated to evaluate the anti-inflammatory efficacy of the extract mixture of the exemplary embodiment.

FIG. 5 shows the results of the measurement of the amount of NO produced in the extract mixture of Example 1. As can be seen from FIG. 5, in the case of the extract mixture of the present disclosure in which the extract of *Atractylodes japonica* Koidz., *Perilla frutescens* Britt. and Acanthopanaxsenticosus are mixed, it could be confirmed that the extract mixture shows a remarkable anti-inflammatory effect as compared with a control without treatment of the extract mixture of the present disclosure. In FIG. 4, negative control used RAW 264.7 cells which were not treated with any extract, and positive control used RAW 264.7 cells which were treated with LPS. It may be confirmed whether the inflammatory effect was reduced or not as compared with the positive control when the extract of Example 1 of the present disclosure was treated.

7. Evaluation of Efficacy Against Arthritis (1) Production of Arthritis Animal Model An arthritic animal model was produced to verify the anti-inflammatory efficacy of the extract mixture of the present disclosure in animal models.

At this time, the arthritic animal model was produced by injecting 2 mg of ArthritoMab antibody cocktail (manufactured by mabioscience) with IP into a Balb/C mouse and injecting 50 ug of LPS with intraperitoneal injection (IP) after 3 days.

(2) Evaluation of Efficacy on Arthritic Animal Model

By using the mouse model obtained in the above (1), the extract mixture of Example 1 and Example 6 of the present disclosure was orally administered at a dose of 25 to 100 mg/kg daily from the day of LPS injection into a mouse, and the degree of thickness and volume of joints were measured.

Figure 6:
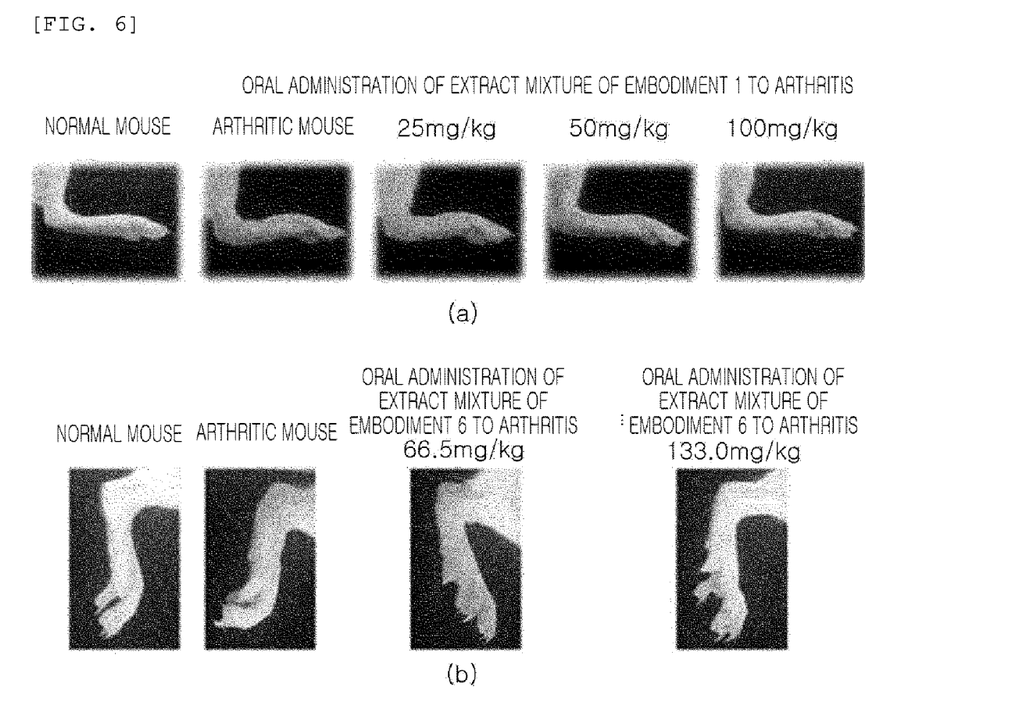
FIG. 6 illustrates changes in hindlimbs after oral administration of an alcohol extract mixture (a) and a supercritical extract mixture (b) of the present disclosure to an arthritic mouse model.

FIG. 6A illustrates changes in the hindlimbs of the actual arthritic mouse model confirmed on the 7th day when the extract mixture of Example 1 of the present disclosure was orally administered at a dose of 25 to 100 mg/kg daily.

As can be seen from FIG. 6, it may be confirmed that the extract mixture of the present disclosure increased the treatment effect of arthritis in a dose-dependent manner, and a visible effect was obtained after 7 days.

On the other hand, FIG. 6B illustrates that the extract mixture of Example 6, in which the supercritical extract of *Perilla frutescens* Britt. and *Atractylodes japonica* Koidz. was mixed at a ratio 1:1, was orally administered daily at a concentration of 66.5, and 133.0 mg/Kg, respectively, and the degree of the thickness and volume of joints were measured on the $6^{th}$ day.

As can be seen from FIG. 6B, it may also be confirmed that the extract mixture showed a dose-dependent increase in the effects of arthritis treatment, and further, the effect of alleviating arthritis seems to be concentration-dependent in the case of an alcohol extract mixture, but the effect is less than that of a supercritical extract mixture.

Figure 7A:
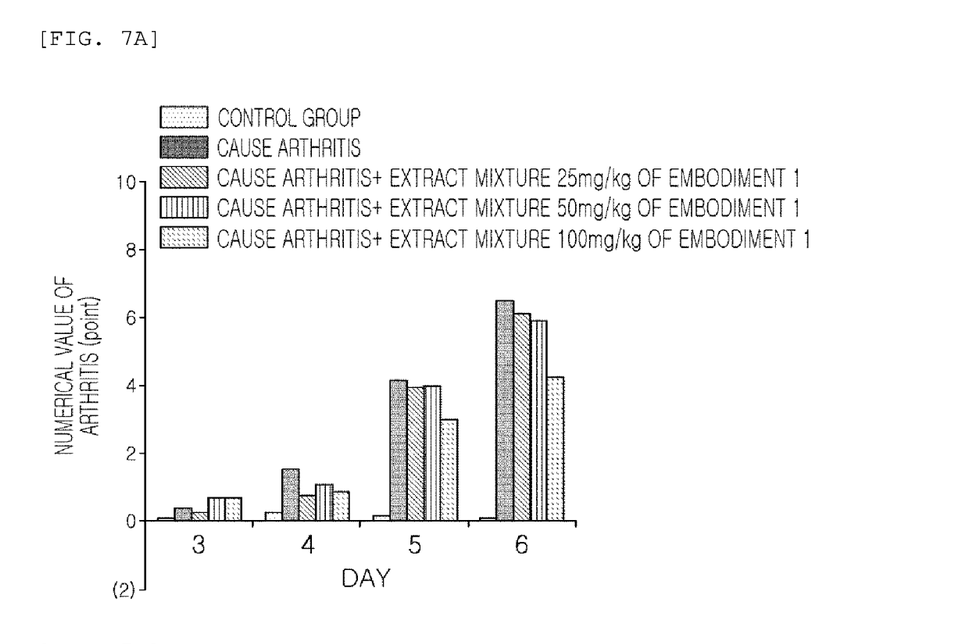
FIGS. 7A to 7C illustrate changes in numerical values of arthritis (a), changes in the thickness of edema of the hindlimbs (b) and changes in the volume of edema of the hindlimbs (c) observed until the sixth day when the extract mixture of Example 1 was orally administered at a dose of 25 to 100 mg/kg to an arthritic mouse model, respectively.
Figure 7B:
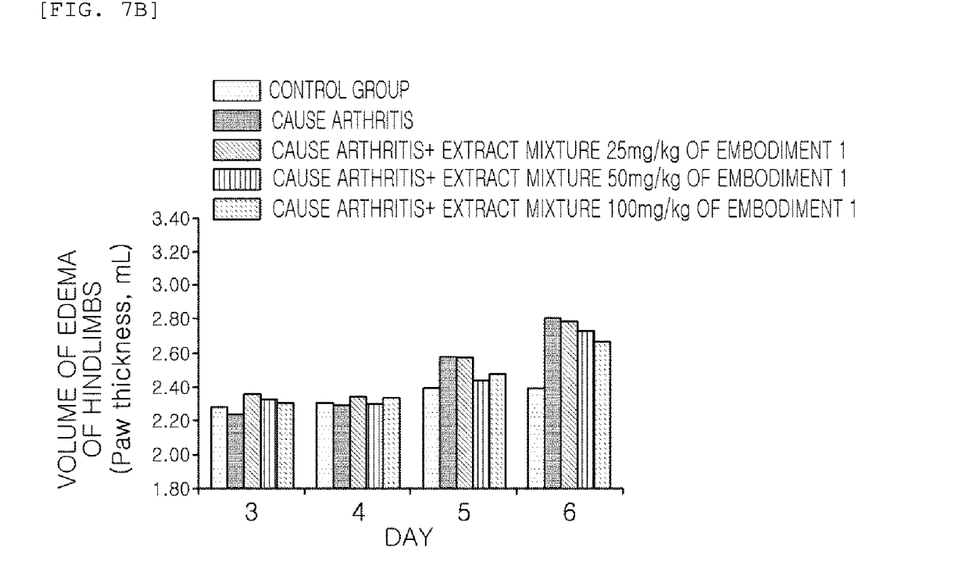
Figure 7C:
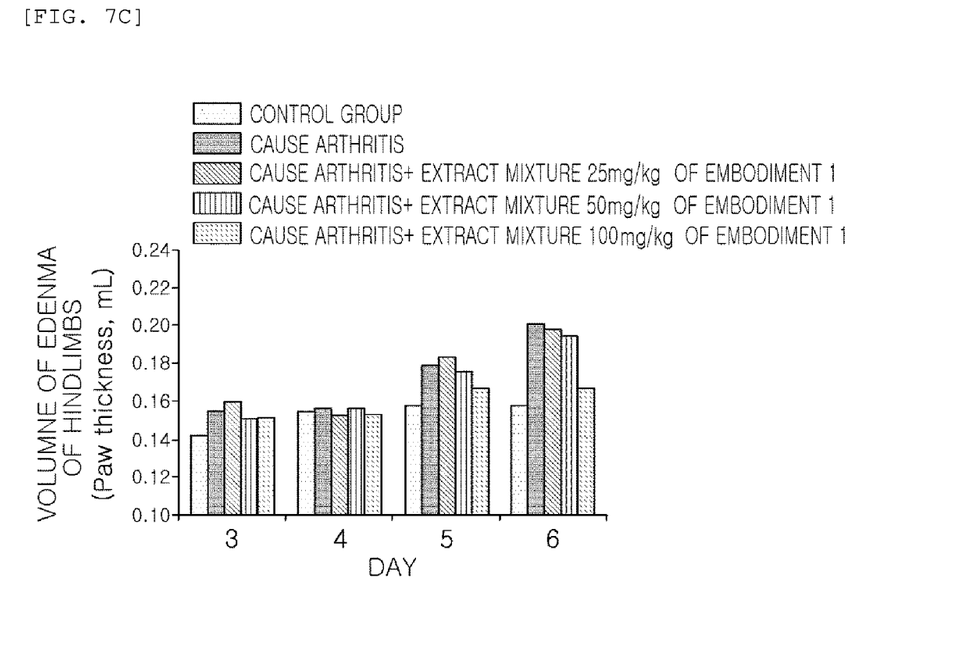

On the other hand, FIG. 7A to 7C illustrate that changes in numerical value of arthritis (a), changes in thickness of edema of hindlimbs (b) and changes in changes in volume of edema of hindlimbs (c) confirmed on the $6^{th}$ day when the extract mixture of Example 1 of the present disclosure was orally administered at a dose of 25 to 100 mg/kg to a mouse model of arthritis, respectively.

As can be seen from FIG. 7, it may be confirmed that the extract mixture of the present disclosure has an effect that the treatment effect of arthritis was increased in a dose-dependent manner.

Figure 8A:
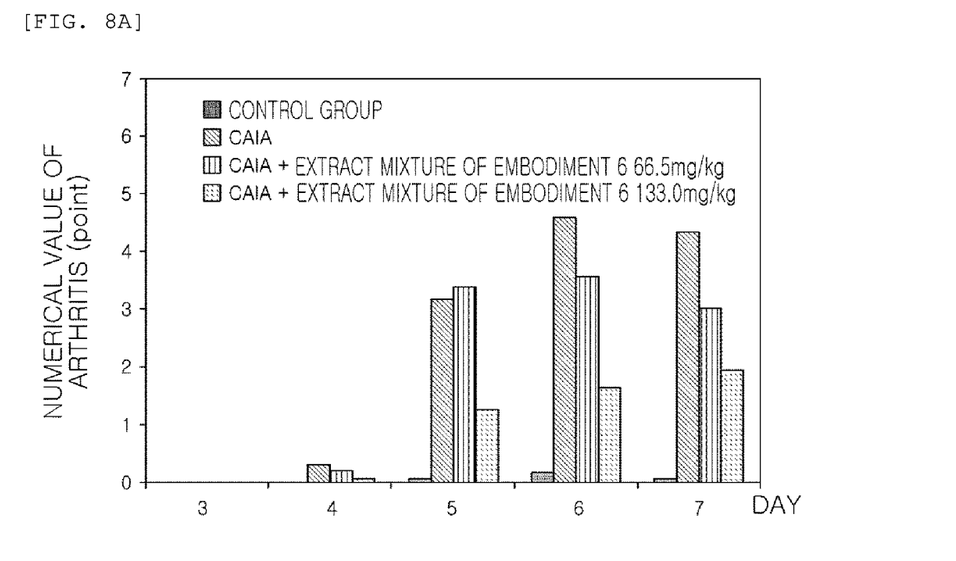
FIGS. 8A to 8C illustrate changes in numerical values of arthritis (a), changes in the thickness of edema of the hindlimbs (b) and changes in the volume of edema of the hindlimbs (c) observed until the seventh day when the extract mixture of Example 6 was orally administered at a dose of 66.5 and 133.0 mg/kg to an arthritic mouse model, respectively.
Figure 8B:
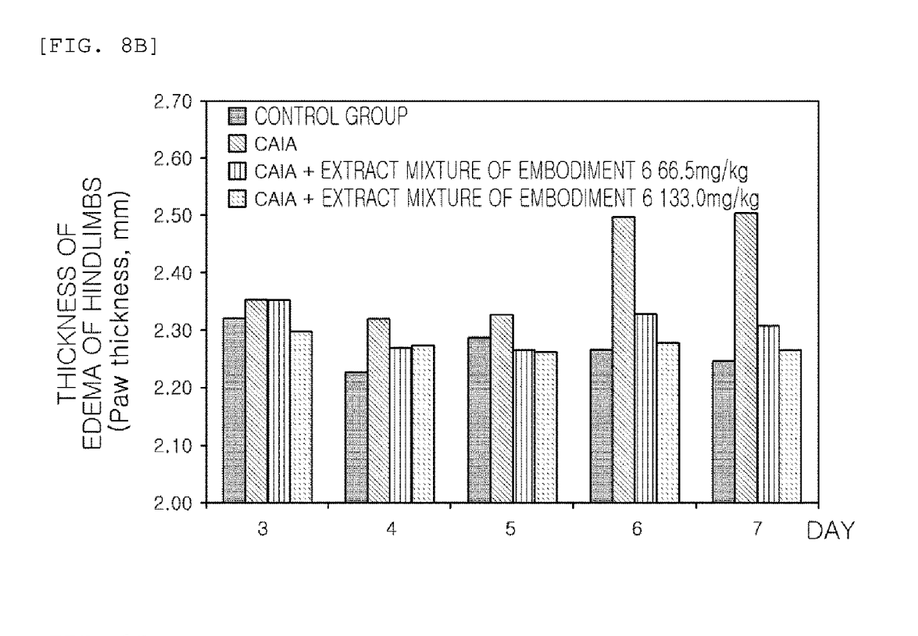
Figure 8C:
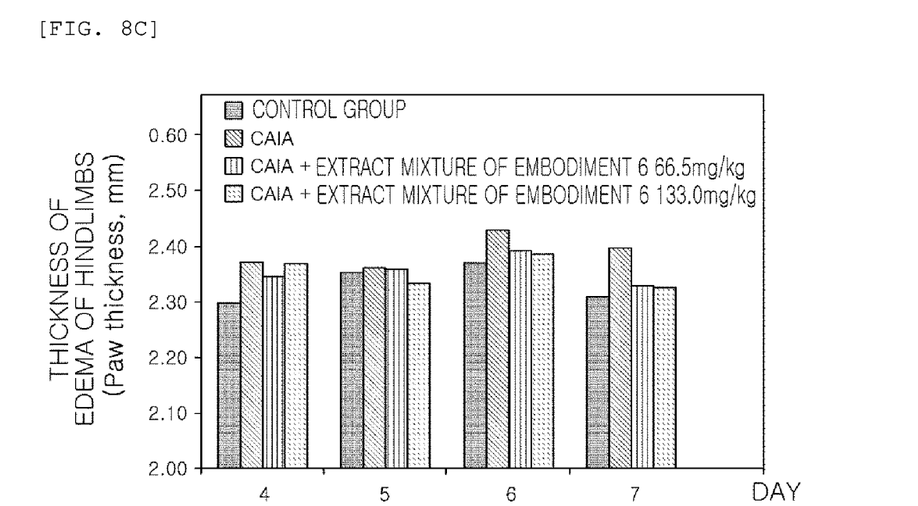

Further, FIGS. 8A to 8C illustrate that changes in numerical value of arthritis (a), changes in thickness of edema of hindlimbs (b) and changes in volume of edema of hindlimbs (c) confirmed until the $7^{th}$ day when the extract mixture of Example 6 of the present disclosure was orally administered at a dose of 66.5 and 133.0 mg/kg to a mouse model of arthritis, respectively.

As can be seen from FIG. 8, it may be confirmed that the extract mixture of the present disclosure has an effect that a therapeutic effect of arthritis is significantly increased when the combined extract obtained by supercritical extraction was used.

While exemplary embodiments have been shown and described above, it will be apparent to those skilled in the art that modifications and variations could be made without departing from the scope of the present invention as defined by the appended claims.

Depositary institution: Korea Research Institute of Bioscience & Biotechnology

The invention claimed is:

1. An anti-inflammatory composition comprising a phyto-extract mixture including an extract of *Perilla frutescens* (L.) Britt. (Accession number: KCTC 13077BP), and an extract of *Atractylodes japonica* Koidz.

2. The anti-inflammatory composition according to claim 1, wherein the extract of *Perilla frutescens* (L.) Britt. (Accession number: KCTC 13077BP) comprises isoegomaketone (IK) or a salt of the isoegomaketone (IK) as an active ingredient.

3. The anti-inflammatory composition according to claim 1, wherein the extract of *Perilla frutescens* (L.) Britt. (Accession number: KCTC 13077BP) has an isoegomaketone (IK) content of 10 mg to 30 mg per 1 g of extract, and an isoegomaketone (IK) concentration of 100 mg/mL to 300 mg/mL.

4. The anti-inflammatory composition according to claim 1, wherein the extract of *Perilla frutescens* (L.) Britt. (Accession number: KCTC 13077BP) and the extract of the *Atractylodes japonica* Koidz. are obtained by alcohol extraction using an ethanol solvent, respectively.

5. The anti-inflammatory composition according to claim 1, wherein the extract of *Perilla frutescens* (L.) Britt. (Accession number: KCTC 13077BP) and the extract of *Atractylodes japonica* Koidz. are obtained by supercritical extraction, respectively.

6. The anti-inflammatory composition according to claim 1, wherein the phyto-extract mixture further comprises an alcohol extract by an ethanol solvent of Acanthopanaxsenticosus.

7. The anti-inflammatory composition according to claim 6, wherein the phyto-extract mixture is formed as the extract of *Perilla frutescens* (L.) Britt. (Accession number: KCTC 13077BP), the extract of *Atractylodes japonica* Koidz. and the extract of Acanthopanaxsenticosus are mixed at a weight ratio of 1:1:1.

8. A method of manufacturing an anti-inflammatory composition including a phyto-extract mixture comprising:
   obtaining phyto-extracts, including obtaining an extract of a *Perilla frutescens* (L.) Britt. (Accession number: KCTC 13077BP) and obtaining an extract of *Atractylodes japonica* Koidz., respectively; and
   manufacturing an extract mixture by mixing respectively obtained the phyto-extracts.

9. The method of manufacturing the anti-inflammatory composition according to claim 8, wherein the respectively obtaining the phyto-extracts is performed by comprising lyophilizing each plant; pulverizing the lyophilized plant; and extracting the lyophilized plant by blending the lyophilized plant with an ethanol solvent, independently.

10. The method of manufacturing the anti-inflammatory composition according to claim 9, wherein the phyto-extract further comprises an Acanthopanaxsenticosus extract.

11. The method of manufacturing the anti-inflammatory composition according to claim 8, wherein the respectively obtaining the phyto-extract is carried out by supercritical extraction of each plant.

12. A pharmaceutical composition for the treatment of inflammatory diseases comprising a phyto-extract mixture including an extract of *Perilla frutescens* (L.) Britt. (Accession number: KCTC 13077BP) and an extract of *Atractylodes japonica* Koidz.

13. The pharmaceutical composition for the treatment of inflammatory diseases according to claim 12, wherein the phyto-extract mixture further comprises an Acanthopanaxsenticosus extract.

14. The pharmaceutical composition for the treatment of inflammatory diseases according to claim 12, wherein the inflammatory diseases are selected from a group consisting of asthma, chronic obstructive pulmonary disease (COPD), allergic rhinitis, dermatitis, arthritis, allergies and inflammatory bowel disease.

15. The pharmaceutical composition for the treatment of inflammatory diseases according to claim 14, wherein the arthritis is rheumatoid arthritis.

16. The pharmaceutical composition for the treatment of inflammatory diseases according to claim 12, wherein the pharmaceutical composition further comprises a pharmaceutically acceptable carrier or excipient.

* * * * *